(12) United States Patent
Rinn

(10) Patent No.: US 9,469,008 B2
(45) Date of Patent: Oct. 18, 2016

(54) APPARATUS FOR MEASURING DRILLING RESISTANCE IN A MATERIAL TO BE EXAMINED

(71) Applicant: Frank Rinn, Heildelberg (DE)

(72) Inventor: Frank Rinn, Heildelberg (DE)

( * ) Notice: Subject to any disclaimer, the term of this patent is extended or adjusted under 35 U.S.C. 154(b) by 135 days.

(21) Appl. No.: 14/586,638

(22) Filed: Dec. 30, 2014

(65) Prior Publication Data

US 2015/0183073 A1    Jul. 2, 2015

(30) Foreign Application Priority Data

Dec. 31, 2013   (DE) .......................... 10 2013 022 241
Dec. 1, 2014    (DE) .......................... 10 2014 017 637

(51) Int. Cl.
*E21B 49/00* (2006.01)
*B23Q 17/09* (2006.01)
*B23B 49/00* (2006.01)

(52) U.S. Cl.
CPC ........... *B23Q 17/0966* (2013.01); *B23B 49/00* (2013.01); *E21B 49/003* (2013.01); *B23B 2270/34* (2013.01); *B23B 2270/483* (2013.01); *G01N 2203/0053* (2013.01); *Y10T 408/05* (2015.01)

(58) Field of Classification Search
None
See application file for complete search history.

(56) References Cited

U.S. PATENT DOCUMENTS

| | | | | |
|---|---|---|---|---|
| 4,785,894 A | * | 11/1988 | Davis, Jr. ................ | E21B 12/02 175/39 |
| 4,785,895 A | * | 11/1988 | Davis, Jr. ................ | E21B 10/22 175/39 |
| 2010/0183389 A1 | * | 7/2010 | Bisiach ................... | B23B 35/00 408/1 R |

FOREIGN PATENT DOCUMENTS

| | | | | |
|---|---|---|---|---|
| DE | 41 22 494 A1 | | 3/1992 | |
| WO | WO 2011090481 A1 | * | 7/2011 | ............. E21B 47/01 |

* cited by examiner

*Primary Examiner* — Andre Allen
(74) *Attorney, Agent, or Firm* — Moore & Van Allen PLLC; Henry B. Ward, III

(57) ABSTRACT

A device for measuring resistance to drilling in a material being investigated, especially wood, with a drilling appliance (1) driving a drill bit (2) into the material and a measuring device for measuring the mechanical resistance to the drill bit (2) upon its penetration into the material, is configured and modified in regard to a secure measurement even in tight space conditions around the material being investigated such that the drilling appliance (1) is coordinated with several U-shaped guide elements (4) which can move along a drilling axis (3) with legs (5, 6) of different length and a base region (7) joining the two legs (5, 6), and in each longer leg (6) a passage (8) is formed for the drill bit (2) in order to guide the drill bit (2).

20 Claims, 3 Drawing Sheets

APPARATUS FOR MEASURING DRILLING RESISTANCE IN A MATERIAL TO BE EXAMINED

Figure 1:
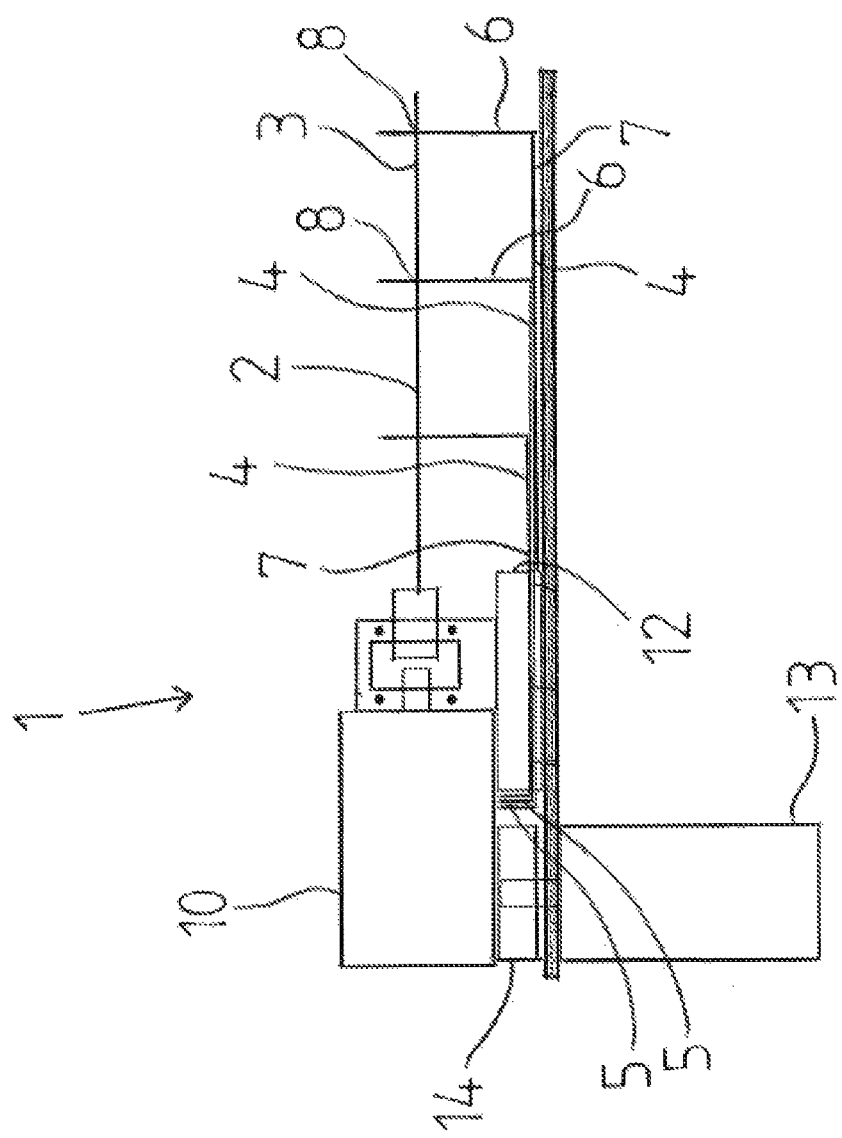

The invention concerns a device for measuring resistance to drilling in a material being investigated, especially wood, with a drilling appliance driving a drill bit into the material and a measuring device for measuring the mechanical resistance to the drill bit upon its penetration into the material.

A device of the aforementioned kind is known for example from DE 41 22 494 A1. The known device for measuring resistance to drilling has a drill bit in the form of a drilling needle, which is driven by means of a drilling appliance into the material being investigated. Furthermore, the known device has a measurement device for measuring the mechanical resistance of the drill bit when it penetrates into the material.

In such a device for drill resistance measurement, the drill bit has a large length, usually corresponding to the desired drilling depth. The drilling depth is often 40 to 50 cm, occasionally more than one meter. Therefore, it is of special importance for the device to guide the drill bit securely during the drilling process and to protect it against buckling. For this, the known device has support elements for the drill bit in the form of extensible and retractable telescopic cylindrical sleeves, having passages for the guiding of the drill bit.

Such a supporting of the drill bit during the drilling process takes up a sizeable space, on account of the length and thickness of the individual telescopic sleeves, and also the ratio of drilling depth to length of the overall device is unfavorable. In other words, the device usually needs to be much longer in its configuration than would be dictated by the drilling depth and the length of the drill bit.

This is unfavorable, inasmuch as the device for an adequate drilling depth of usually 40 to 50 cm overall still needs to be as short as possible in order to be used around a material being investigated even in tight quarters. For example, when investigating ceiling beams of a wooden structure the space is usually confined, so that the shortest possible device is desirable.

Furthermore, the drill bit in the aforementioned telescopic guide is not visible, and so it cannot be observed and controlled both during the measurement process and during servicing work. Therefore, fractures or bending of the drill bit cannot be identified in good time and often lead in practice to damaging of the device, and not just the telescopic guide.

Therefore, the problem of the present invention is to configure and modify a device of the kind mentioned above with simple design features so that a secure measurement is made possible in a material being investigated even when space is confined around the material being investigated.

According to the invention, the above problem is solved by a device with the features of claim 1. Accordingly, the device is configured and modified so that the drilling appliance is coordinated with several U-shaped guide elements which can move along a drilling axis with legs of different length and a base region joining the two legs, and in each longer leg a passage is formed for the drill bit in order to guide the drill bit.

First of all, it has been discovered as an inventive step that a structure with bulky nested telescopic sleeves is not required for the secure supporting of a drill bit during a drilling process. In a further inventive step, it was then realized that the aforementioned problem is solved in surprisingly simple fashion by the realization of several U-shaped guide elements able to move along a drilling axis, which have legs of different length and a base region joining the two legs, while in each longer leg there is formed a passage for the drill bit in order to guide the drill bit. The configuration of the guide elements in a U-shape enables a substantially more space-saving arrangement of the guide elements relative to each other and in a housing of the device than is possible with cylindrical telescopic sleeves, while at the same time a continual observation and control of the drill bit is made possible—from the side in the U-shaped guide elements—especially in the case of a transparent design of at least parts of the external housing, so that one can respond at once to bit bending or breakage and prevent damage to the drilling appliance as well as substantially facilitate the servicing. With a suitable arrangement and configuration of the U-shaped guide elements, these can be pushed together in the situation of a drill bit introduced as far as possible into the material so that ultimately only the thickness of the leg having the passage for the drill bit dictates the drilling depth of the drill bit. For a suitably thin configuration of the leg having the passage for the drill bit, this usually produces a much smaller loss of drill depth than is produced by the height of a cylindrical telescopic sleeve in the known device.

Consequently, the device according to the invention can be shorter in configuration than the device known from the prior art and it thereby achieves a much better stroke to length ratio.

Consequently, with the device according to the invention there is provided a device in which a secure measurement is made possible with simple design features in a material being investigated, even with the space conditions are tight around the material being investigated.

In regard to an especially space-saving arrangement of the guide elements, the guide elements can each have base regions of different length and be arranged one in the other. By arranging the guide elements one in the other, the result is an arrangement of the guide elements with base regions arranged one on top of the other. In this position arranged one in the other or one above the other the guide elements can be shifted along the base regions and along a drill axis in the device. In this way, the longer legs, all of which protrude in the same direction and are arranged essentially parallel to each other, form by their passages formed in the legs a guide region for the drill bit.

In regard to a secure and controlled displacement of the guide elements during a drilling process, the guide elements are guided by a common guideway. This guideway is advantageously formed from a plastic which has a self-lubricating quality.

For the secure guidance of the guide elements along or parallel to the drilling axis, the guideway can have the shape of a rail. The guideway here can extend along the drilling axis or parallel to the drilling axis, preferably along the entire range of movement of the guide elements.

Furthermore, in regard to an especially secure guidance of the movement of the guide elements, the guideway can have a recess for the guide elements. All the guide elements can extend into such a recess—for example, by their base region. All the base regions can be arranged one above the other in this recess so that the guideway can guide all the guide elements together. In an especially advantageous configuration, the recess can have a trapezoidal cross section.

In this context, the base regions of the guide elements can have different widths, adapted to a shape of the recess. For example, in the case of a trapezoidal cross section of the recess, when the base regions of the guide elements are arranged one above the other in the recess, a lower guide element can have a greater width than the guide elements arranged above it, in order to fill out the region of greatest width in the trapezoidal cross section. In this regard, the width of the base regions of individual guide elements can decrease from a lower guide element to an upper guide element, namely, it can be adapted to a trapezoidal cross section which has a continuously decreasing width starting from a broad region and ending at a narrow region.

Such a trapezoidal recess, which can extend along the entire rail-shaped guideway, thus forms a secure and also vibration-dampening guideway for the guide elements in each relative position of displacement of the guide elements from each other, while in each position a fluttering of the individual guide elements is prevented by the limiting of the motion of the guide elements in the trapezoidal guideway. Consequently, with such a trapezoidal cross section of a recess of the guideway in conjunction with guide elements with adapted widths of the base regions, an especially secure guidance of the guide elements is assured in every position of displacement and, thus, operating position of the device.

All the legs of the guide elements can have the same width, which affords the possibility of being led through a nearly rectangular recess region in the guideway that can extend along the entire guideway and thus along an entire movement range of the guide elements. The legs of the guide elements are then led securely in the recess region adapted to the width of the legs. The width of the recess region can be constant along its entire length and be only slightly broader than the width of the legs.

In order to assure a secure displacement of the guide elements that is adapted to the progressing drilling process, a slide coupled to the drill bit and able to move during a drilling process can be arranged at least partly between the legs of an uppermost guide element. Thanks to a moving of the slide and thus a movement of the drill bit into the material, the guide elements are gradually displaced in the drilling direction—as the drilling proceeds. With this, the slide arranged in the uppermost guide element carries along nearly all the guide elements during its displacement in the drilling direction, so that upon reaching the maximum drilling depth the longer legs of the guide elements all abut against each other.

During a backward movement of the slide, for example to pull the drill bit out from the hole produced, the slide first of all pushes against the shorter leg of the uppermost guide element and then gradually against the shorter legs of the guide elements arranged beneath the uppermost guide element until ultimately all guide elements are moved into their maximum retracted position, in which all the shorter legs of the guide elements lie against each other at the end region of the device, facing away from the region of emergence of the drill bit from the device. In this situation, the longer legs of the guide elements have a definable spacing from each other, corresponding to the length of the base regions of the individual guide elements, in order to securely support the drill bit, located essentially entirely in the device, in these definable, preferably regular intervals of the longer legs. When a drilling process is started from this position, the drill bit is consequently guided along its entire length through the longer legs of the guide elements, arranged at regular intervals. The length of the longer legs is different from one guide element to another, where the longer leg of an uppermost guide element is the shortest long leg and the longer leg of a lowermost guide element is the longest long leg. In advantageous manner, the upper edges of the preferably rectangular longer legs lie in a common plane.

In analogous manner, the shorter legs of guide elements arranged one in another or one above another are also of different length, where the again preferably rectangular shorter legs have upper edges which lie in a common plane. It should be observed in regard to the longer legs that the passages for the drill bit are formed in such positions of the legs that these passages of all the longer legs are flush in the state of the guide elements arranged one in another or one above another, in order to allow the drill bit to be inserted through all the passages.

In an advantageous manner, the slide is likewise guided by the guideway during a movement of the slide. In this regard, the guideway can take on a dual function in especially advantageous manner, namely, on the one hand a guideway for the guide elements and on the other hand a guideway for the slide. For this, the slide can in advantageous manner have essentially a C-profile shape, namely, in order to reach around a preferably rail-shaped guideway from the top. In this respect, an essentially rectangular shape of the guideway is advantageous, in order to allow the reach-around by the C-profile shape of the slide. In this way, the slide is guided along its entire movement stretch not only in the lateral direction, but also prevented from lifting off from the guideway, so that the drill bit is driven and moved solely in axial manner, which has critical influence on the precision of the measurement values being registered.

In regard to an especially secure and reliable drive for the slide, the slide can be coupled by a cable or a belt, preferably a V-belt, to a feed mechanism or a drive wheel of a feed mechanism. The coupling of the slide to the feed mechanism or a drive wheel of the feed mechanism by a cable or a belt affords the special advantage that the cable or the belt upon malfunction or jamming of the slide usually enables a slip through in the sense of a slip coupling relative to the feed mechanism or the drive wheel, with no fear of further damage, such as is the case with a traditional spindle drive. Accordingly, the coupling of the slide by means of a cable or a belt according to the invention affords an especially safe operation of the device.

By suitable choice of the material of the slide, e.g., refined steel or anodized aluminum, a slight friction is accomplished, and one which is uniform especially along the drilling path. Only such a preferably lubricant-free sliding guideway of the guide elements and the slide enables virtually maintenance-free applications at extreme temperatures, for example, when investigating wooden structures (bridges, poles) or trees at high or low external temperatures. Since oftentimes shavings or fine drill dust get into the device during the measurement processes, this often leads to technical problems and measurement inaccuracies in the case of feed designs with spindles and lubricants, especially in combination with extreme temperatures, since the motor power is measured and recorded as an indication of the mechanical resistance to penetration, or even to a premature failure.

In regard to an especially secure operation of the device, the device can have a housing to accommodate at least partly the drilling appliance and the measurement device in the housing, wherein the housing can be made of an electrically nonconducting and/or slightly thermally conducting material, preferably a plastic. The accommodating of the drilling appliance and the measurement device in the housing first of all affords a protection against external influences and contamination. The forming of the housing from an electrically nonconducting and slightly thermally conducting material affords the advantage of protecting the operator in event of an unintentional drilling through electrical power lines in a material being investigated. On the other hand, a slightly thermally conducting housing is advantageous for handling at low external temperatures, since the device or the housing must often be grasped with the bare hands during use in order to ensure a secure operation of control elements of the device. Making the housing of plastic ensures that these requirements are met.

In another advantageous way, the housing can be made transparent at least in some areas. Such a transparent design allows for visual checking of the drilling process and thus a rapid intervention in event of a malfunction, for example, a jamming of the drill bit. In this way, one can often avoid damage to the device. In one preferred embodiment, the housing has two half shells, which enable an easy assembly of the housing around the drilling appliance and measurement device. In the case of such a design, an upper half shell of the housing can preferably be made transparent, in order to afford the already mentioned benefits of such a transparent design.

Basically it should be noted in this place that the design of the device with an at least partly transparent or entirely transparent housing—as described above—can essentially be done independently of the design of the device with the previously specified U-shaped guide elements. In other words, the at least partly transparent design of the housing is also advantageous for devices of this kind that have any given guideway mechanisms for the drill bit.

In such a housing at least one window-like passage can be formed, preferably with marginal areas or edges of the at least one passage at least partly beveled toward the inside of the housing. Such a window-like passage allows for easy access to the interior of the housing and, thus, to the drilling appliance and/or measurement device.

In another advantageous manner, the at least one passage can be closed at least in some places. Preferably, a transparent plate can be coordinated with the at least one passage for the at least partial closure of the at least one passage. In the case of a nontransparent housing, such a plate alone can be transparent, to enable a visual checking of the inside of the housing.

In another advantageous manner, the drilling appliance and the measurement device can be arranged on a common carrier element, wherein the housing in advantageous manner can be fastened to the carrier element. Thus, the carrier element forms the support structure of the device, while the housing can be arranged merely as an external protection, without the housing providing any support function. Such a carrier element can be fashioned as a T-profile or U-profile and/or be made of metal, especially aluminum. A profiled configuration of the carrier element affords an especially high stability of the device overall.

When such a carrier element is provided, at least one passage can be formed in the carrier element corresponding to the at least one passage in the housing. In this way, a visual checking can be assured through the passage in the housing and the passage in the carrier element of areas of the device located further inward.

In another advantageous embodiment, a motor and/or a gearing of a feed mechanism for the drill bit can be arranged at least partly in a handle arranged on the housing and/or on the carrier element. The arrangement in the handle affords a secure and space-saving arrangement.

In regard to a comfortable handling of the device, a cushioning can be arranged at one end or region of the housing opposite the region of emergence of the drill bit from the housing. Since the device usually has to be pressed against the material being investigated during a drilling process, such a cushioning is advantageous and comfortable to the user, especially when the device has to be pressed against the material in unfavorable space conditions, for example, by the knee of the user.

In another advantageous manner, a handle arranged on the housing and/or on the carrier element can be coordinated with a camera for the documentation of a drilling process, wherein advantageously the camera can be fastened to the handle or integrated or installed in the handle. In another advantageous manner, the camera can be automatically activatable during a drilling process.

Such a camera offers major benefits in particular during the following scenario:

In many measurements, not only on wooden power line poles, but also for roadside trees and wooden toys, it is important and often critical, especially during subsequent legal disputes after accidents, to be able to document precisely where and how the measurement was done. If one is making a borehole with the device, one usually does not have any hand free for the photography operation. It is then often difficult afterwards to reconstruct the exact attitude of the device during the drilling process. But this attitude is critical to the representation of the measurement profiles taken. Even slight angle deviations during the measurements can lead to fundamentally different, sometimes even unusable measurement profiles and thus faulty judgments as to the strength/stability of a material or structure being investigated.

To solve this problem, a camera can be arranged or installed, for example, at the lower end of a handle—preferably beneath a handle shell, which can photograph or even film the drilling process. From this installed position, the investigated object and the particular drilling point can usually be well viewed with a sufficiently wide-angle optics. By means of automatic coupling to an electronics of the drill, the starting and stopping of the camera can be related to the registration of a measurement profile, so that when needed the entire drilling process can also be documented. Thanks to the always identical perspective and the distance from the drilling position as defined by the installation position of the camera, photos or films are always scaled the same and can be measured and compared in terms of distance and angle.

There now exist various ways of configuring and modifying the teaching of the present invention in advantageous manner. For this, reference is made on the one hand to the following claims and on the other hand to the following discussion of preferred sample embodiments of the invention with the aid of the drawing. In connection with the discussion of the preferred sample embodiments of the invention with the aid of the drawing, generally preferred configurations and modifications of the teaching will also be explained. In the drawing are shown FIG. 1 in a schematic side view, a sample embodiment of a device according to the invention, FIG. 2 in a magnified and sectioned schematic representation, the sample embodiment of FIG. 1 and FIG. 3 in a schematic side view, another sample embodiment of the device according to the invention.

FIG. 1 shows in a schematic side view a sample embodiment of a device for drill resistance measurement in a material being investigated. The device has a drilling appliance 1 for driving a drill bit 2 in the form of a drilling needle, for example, into the material. In regard to a secure supporting of the drill bit 2 during a drilling process, the drilling appliance 1 is coordinated with three U-shaped guide elements 4 movable along a drilling axis 3 and having legs 5, 6 of different length and a base region 7 joining the two legs 5, 6. In each longer leg 6 there is formed a passage 8 for the drill bit 2 to guide the drill bit 2. The drill bit 2 extends through all the passages 8 of the guide elements 4.

The guide elements 4 each have base regions 7 of different length and are arranged one in another and one above another. The guide element 4 with the shortest base region 7 is the uppermost guide element 4 and the guide element 4 with the longest base region 7 is the lowermost guide element 4. The guide elements 4 are led through a common guideway 9, shown in detail in FIG. 2, which shows a magnified schematic cross section through the device shown in FIG. 1.

The guideway 9 has a rail shape and extends along the entire movement range of the guide elements 4, that is, essentially along the entire lengthwise dimension of the device.

Figure 2:
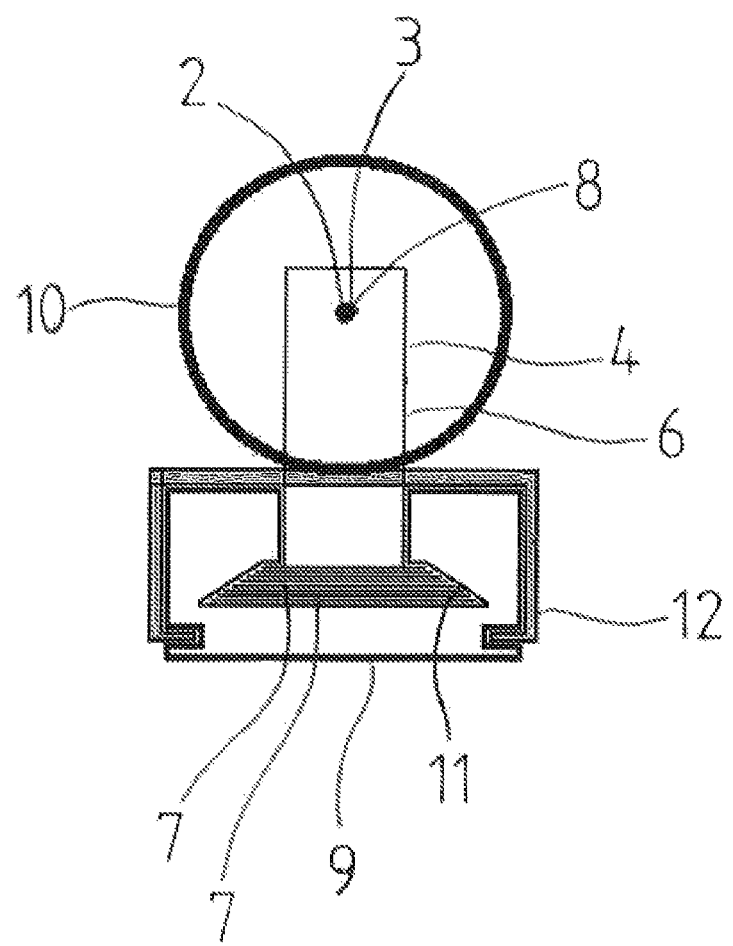

The guideway 9 has a recess 11 for the base regions 7 of the guide elements 4, and the recess 11 has a trapezoidal cross section. The base regions 7 of the guide elements 4 each have different widths, adapted to the shape of the recess 11, while on the other hand all the legs 5, 6 of the guide elements 4 have the same width. In FIG. 2 it can be seen in this regard that all the guide elements 4 with their base regions 7 of different width are arranged in the trapezoidal recess 11 of the guideway 9. The legs 5 and 6 of the guide elements 4 extend through a rectangular guideway region of the guideway 9 and are securely guided through this guideway region during the movement process of the guide elements 4. A slide 12 coupled to the drill bit 2 and able to move during a drilling process is arranged at least partly between the legs 5, 6 of an uppermost guide element 4. During movement of the slide 12, the slide 12 is likewise guided by the guideway 9. For this, the slide 12 has a C-profile shape, in order to reach around the guideway 9 or engage with recesses or grooves of the guideway 9, as shown in FIG. 2.

The slide 12 is coupled by a V-belt, not shown here, to a feed mechanism 13 or, more specifically, to a drive wheel 14 of the feed mechanism 13.

Figure 3:
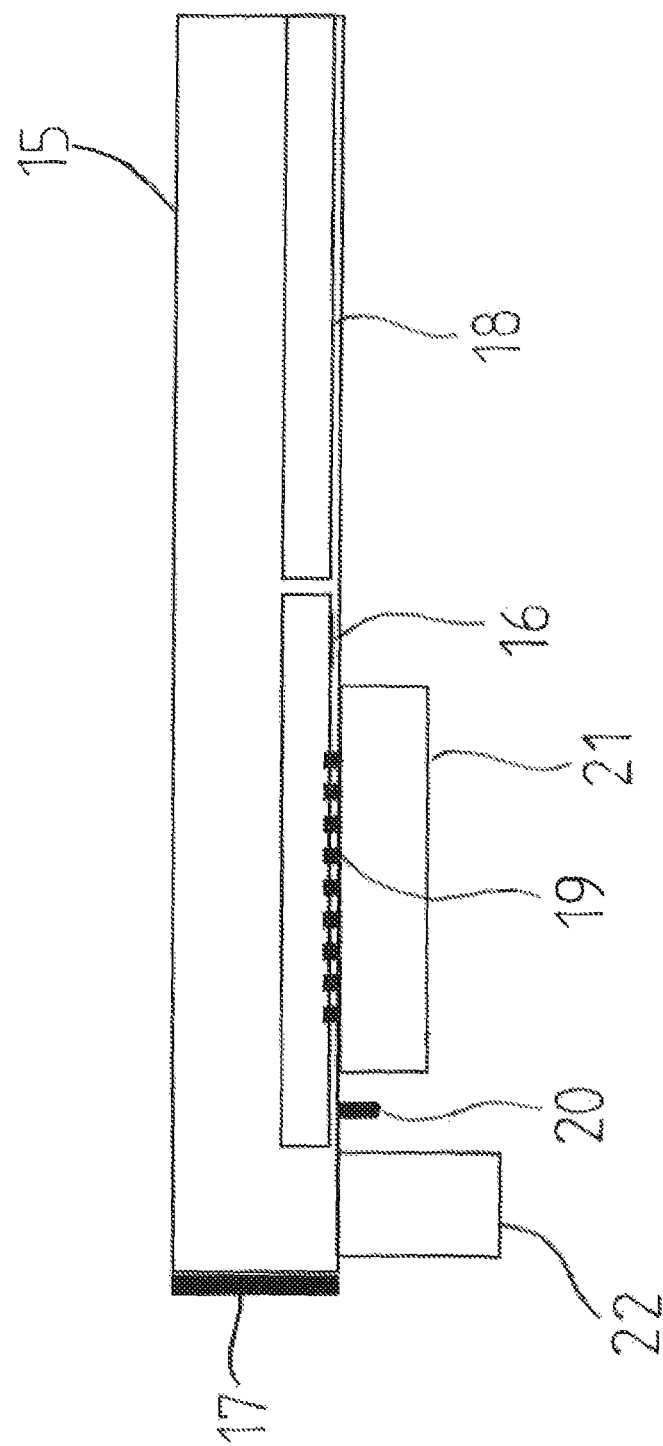

FIG. 3 shows in a schematic side view another sample embodiment of a device according to the invention, where the device has a housing 15 for at least partial accommodation of the drilling appliance 1 and the measurement device 16 in the housing 15. The housing 15 is made of an electrically nonconducting and slightly thermally conducting material. The material is a plastic.

The housing 15 is transparent and has a cushioning 17 at its back end.

Furthermore, a battery 18 is provided in the housing for a power supply. The device moreover has a control element 19 and a switch 20 for turning the device on and off. Moreover, two handles 21 and 22 are arranged on the housing 15 for handling the device.

In one advantageous configuration, the device has an electrically nonconducting and slightly thermally conducting plastic housing 15. A carrier element arranged inside the housing performs various duties. On the one hand, it carries the essential mechanical components, which are thus independent of the housing 15, and this in turn increases the stability and durability of the device, since external mechanical forces—such as impacts—act first and foremost on the housing and not on the internal construction.

Furthermore, the carrier element enables an external assembly process and thus a low-cost production. Moreover, it divides the interior space into two or more regions and can thus shield the electronics from stray fields of a preferably electrical motor 10, when these are arranged in different regions.

A preferably transparent plate can be inserted into a window in the housing, with beveled edges for example. Such a window makes it possible to change the drill bit in virtually any position of the motor, even when the drill bit 2 has broken off in the drilling appliance 1. In event of greater damage, the user can even replace a drill chuck through the window.

The advancement of the slide 12 occurs preferably by a combination of motor and gearing in the form of the feed mechanism 13. This is placed at the back end of the carrier element, which also affords the structural advantage of hiding the feed mechanism 13 in the handle 22 which is necessary in any case. Furthermore, in this way the drive wheel 14 can be arranged behind the guideway rail 9 and beneath the drill motor 10, so that there is no stroke loss. The feed mechanism 13 fits behind the rail-shaped guideway 9 and thus also under the moving motor 10 so that it causes no stroke loss for the same or comparable external dimensions and does not increase the length or external dimension of the device or its housing 15.

Thus, the stroke to length ratio is significantly increased in that the motor 10 turning the drill bit 2 is arranged on the slide 12 and the feed mechanism 13, or motor and gearing unit, which drives the slide 12 is mounted perpendicular to the drilling axis 3, so that the drive wheel 14 sits behind the rail-shaped guideway 9 and the motor 10 can travel over it. Thus, the feed mechanism 13 does not cause further stroke loss for the same device length or housing length—as with the designs of the prior art. If the motor and gearing unit or feed mechanism 13 providing for the advancement is integrated in the preferably pistol-shaped handle 22, which is advantageous for an optimized handling, it does not result in a stroke loss or any other negative external size increase, but rather "hides" almost unnoticed in the structural parts or design elements and their dimensions which are preferably required any way.

By the drive wheel 14, the slide 12 is moved back and forth, preferably by V-belt or cable drive. This type of drive not only has the advantage of less weight, especially as compared to spindles, but also the advantage that no lubrication is needed, and that an internal mechanical safety can be built in through the choice of the tensile strength of the belt or cable, so that the device when overloaded does not destroy any mechanical components, as is quite common with the previous and current spindle drives.

The slide 12 carrying the drilling appliance 1 and thus also the motor 10 is fashioned as a C-profile, which performs several tasks in connection with the rail-shaped guideway 9: axial guidance of the motor 10, absorbing of the torque produced by the drilling process, and entrainment of the guide elements 4 during forward and backward movement.

The guide elements 4 are fashioned as guide plates, which are bent into a U with legs 5, 6 of unequal length and a base region 7, so that they have in the front area the passage 8 for the drill bit 2 and in the rear area they are retracted by the slide 12 via the leg 5.

The guide elements 4 fashioned as guide plates are made from a stainless spring steel. The length and height of the guide elements 4 are chosen so that the maximum drilling depth is reached with the fewest possible plates. As an example, nine plates with length differences of the base regions 7 of 50 mm each have proven to work well, so that the drill bit 2 is guided or supported every 50 mm.

On the slide 12 there are arranged end switches, which are actuated by the cable leading any way to the motor 10, so that no other cables need to be laid in the device.

The handle 21 covers the display and control elements 19 not needed during normal operation, yet absolutely required in special cases. These include: presetting of the maximum drill depth, presetting of the maximum rate of feed, further printing of the measurement profile of the preceding drilling/measurement process, next feed, retraction without drill bit rotation, and drill bit rotation without feed. Furthermore, LEDs can be provided for status displays.

The switch 20 is located directly in front of the handle 22, so that it can be operated intuitively and without visual checking, and to be protected against mechanical forces. The cushioning 17 enables a comfortable contact with the back side of the device, in order to apply the necessary pressure during a measurement.

With the device according to the invention it is possible to achieve a very light, small and low-cost device with maximum possible precision and durability, while at the same time having the best handling qualities and the best stroke to length ratio achieved thus far.

The guideway 9 is advantageously made from a special, self-lubricating plastic, such as polyamide 6G oil, so that metal can slide along it almost free of friction and lubrication. In this way, both the guide elements 4 and the slide 12 are guided in excellent manner.

So that the guide elements 4 cannot buckle either to the side or perpendicular to the drilling axis 3 and in particular not flutter on account of the high speed of rotation of the drill bit 3, the guideway 9 has a recess 11 with a special trapezoidal cross section, which on the one hand affords the best possible sliding qualities and on the other hand guides the guide elements 4 as rigidly as possible.

In the region where all the base regions 7 of the guide elements 4 lie one above the other, the base regions 7 are fixed relative to each other and thus prevent a fluttering. However, in the regions where they do not overlap each other, or only a few do so, these base regions 7 would flutter if they were not individually guided and prevented from fluttering.

For this, a trapezoidal shape of the recess 11 has been chosen, ensuring that the guide elements 4 are individually smoothly guided. The base regions 7 of the guide elements 4 have different widths, while the lowermost guide element 4 has the base region 7 with the greatest width. In order for the guide elements 4 to move back and forth with the motor 10 on the slide 12 and the drill bit 2 and be guided with smooth running, the curved part of all guide elements 4 or all legs 5 and 6 of all guide elements 4 have the same width, being guided at the side in the upper rectangular opening of the guideway 9. So that the guide elements 4 do not tilt sideways even under heavy load due to the fast turning drill bit 2 with a tendency to buckle when drilling into wood, for example, the lower parts of the guide elements 4, i.e., the die base regions 7, have a wider step, which accomplishes a larger lever for their tilt prevention against the sloping inner flanks of the trapezoidal recess 11. The downwardly increasing width of the base regions 7 ensures an optimal smooth running and continual guidance even in the segments where few of the base regions 7 lie one above the other, since the uppermost base regions 7 are shorter by design and the lowermost base region 7 is the longest. Without any covering by the upper base regions 7 and without the lateral guidance by the sloping inner flanks of the trapezoidal recess 11, the guide elements 4 would flutter, possibly tilt, and be subjected to much greater wear.

Finally, the design of the invention achieves an especially high measurement precision.

Contamination occurs frequently in drill resistance measurements and often adheres firmly to the drill bits 2. This holds especially for the investigation of tree species containing resin or rubber. The contamination can build up in the housing and lead to impaired operation.

Due to the high speed of rotation and the substantial feed rate, the opening of the drill around the drill bit 2 cannot be sealed tight. There must always remain a certain gap, so that no additional and thus disruptive friction forces arise there during the drilling. Thus, the aforementioned contamination necessarily gets into the drill. On the other hand, such contamination will be stripped off inside the drill by the guide elements 4, which prevent a buckling during the forward drilling.

Thus, over time, there is an unavoidable fouling of the inside of the tool, which impairs both the technical functionality and accuracy of the measurement and shortens the lifetime of the tool. To solve this problem, the housing is made at least partly transparent, for example, an upper half shell of a housing can be transparent and the lower half shell of the housing is not transparent. Such a housing can have reclosable passages, so that on the one hand the degree of fouling can be continuously judged visually and on the other hand the dust and grime can be shaken out or removed as needed.

The transparent housing brings further major advantages. Already during the measurement one can see how it is going and whether bending of the drill bit 2 or other disruptions/irregularities are taking place. Furthermore, the measurement process can be shown directly and graphically to the interested party, so that it is not a "black box", but instead a transparent process, which usually increases the trust in a previously unknown method. If a drill bit 2 breaks off in the drill, this is visible at once, which produces further advantages. The measurement can be halted at once in order to prevent damage in the drill. The continuing of a drilling process with broken-off drill bit 2 in the drill usually leads to damage to the drill bit guideway and other components in the drill. A broken-off drill bit 2 can be replaced at once. At the motor 10, a display fastened to and running along with the motor 10 can show information about the measurement, which is visible thanks to the transparent housing 15, yet protected against environmental influences. A display in the drill can show the measurement profile, even on the same scale, yet it is protected by the transparent housing 15.

In regard to further advantageous configurations of the device of the invention, refer to the general part of the specification and to the appended claims, in order to avoid repetition.

Finally, it should be pointed out expressly that the above described sample embodiments of the device according to the invention only serve to explain the claimed teaching, but do not confine it to the sample embodiments.

LIST OF REFERENCE NUMBERS

1 Drilling appliance
2 Drill bit
3 Drilling axis
4 Guide element
5 Leg
6 Leg
7 Base region
8 Passage
9 Guideway 10 Motor
11 Recess
12 Slide
13 Feed mechanism
14 Drive wheel
15 Housing
16 Measurement device
17 Cushioning
18 Battery
19 Control element
20 Switch
21 Handle
22 Handle

The invention claimed is:

1. A device for measuring resistance to drilling in a material being investigated, comprising:
 a drilling appliance for driving a drill bit into the material, the drilling appliance defining a drilling axis, the drilling appliance comprising a plurality of guide elements structured to move along the length of the drilling axis, each guide element comprising a pair of legs of different length, the drilling appliance further comprising a base region joining the pair of legs, each longer leg of each guide element comprises a passage therethrough for the drill bit in order to guide the drill bit; and
 a measuring device for measuring the mechanical resistance to the drill bit upon its penetration into the material.

2. A device according to claim 1, wherein the guide elements each have base regions of different length and are arranged one in the other.

3. A Device according to claim 1, wherein the guide elements are guided by a common guideway.

4. A device according to claim 3, wherein the guideway comprises a rail and the guideway extends along the length of the drilling axis, parallel to the drilling axis.

5. A device according to claim 3, wherein the guideway defines a recess for the guide elements.

6. A device according to claim 5, wherein the recess has a trapezoidal cross section.

7. A device according to claim 5, wherein the base regions of the guide elements have different widths, each base region adapted to the shape of the recess.

8. A device according to claim 1, wherein all the legs of the guide elements have the same width.

9. A device according to claim 1, wherein the width of the base regions of the plurality of guide elements decreases from a lower guide element to an upper guide element.

10. A device according to claim 1, wherein the drilling appliance further comprises a slide coupled to the drill bit and structured to move during the drilling process, wherein the slide is arranged at least partly between the legs of the uppermost guide element.

11. A device according to claim 10, wherein the guide elements are guided by a common guideway and wherein the slide is guided by the guideway upon movement of the slide.

12. A device according to claim 11, wherein the slide has a C-shaped cross section.

13. A device according to claim 10, wherein the drilling appliance comprises a feed mechanism and coupling member, and wherein the slide and feed mechanism are coupled via the coupling member.

14. A device according to claim 10, wherein the coupling member comprises a cable, belt, or a V-belt.

15. A device according to claim 10, wherein the feed mechanism comprises a drive wheel.

16. A device according to claim 1, further comprising a housing (15) for at least partially enclosing the drilling appliance and the measurement device in the housing.

17. A device according to claim 16, wherein the housing is made from a material with at least one of a low electrical conduction and a low thermal conduction.

18. A device according to claim 16, wherein the housing is made from plastic.

19. A device according to claim 16, wherein the housing is at least partially transparent in some regions.

20. A device according to claim 16, wherein the housing defines an upper half-shell that is transparent.

* * * * *